United States Patent [19]

Kawai

[11] Patent Number: 5,423,092

[45] Date of Patent: Jun. 13, 1995

[54] GOGGLES AND SUNGLASSES

[75] Inventor: Hiromitsu Kawai, Osaka, Japan

[73] Assignee: Axe Co., Ltd., Osaka, Japan

[21] Appl. No.: 39,231

[22] PCT Filed: Aug. 10, 1991

[86] PCT No.: PCT/JP92/01033

§ 371 Date: Apr. 20, 1993

§ 102(e) Date: Apr. 20, 1993

[87] PCT Pub. No.: WO93/04392

PCT Pub. Date: Mar. 4, 1993

[30] Foreign Application Priority Data

Aug. 23, 1991 [JP] Japan .................. 3-074691 U

[51] Int. Cl.6 ........................................ A61F 9/02
[52] U.S. Cl. ............................... 2/441; 2/447; 351/44; 351/92
[58] Field of Search ............... 2/441, 443, 447, 432, 2/426, 449, 451; 351/90, 91, 92, 44, 47

[56] References Cited

U.S. PATENT DOCUMENTS

| | | | |
|---|---|---|---|
| 2,921,500 | 1/1960 | Gell | 351/90 X |
| 3,081,461 | 3/1963 | Gurtowski | 2/441 |
| 3,542,460 | 11/1970 | Smith et al. | 351/92 |
| 4,630,321 | 12/1986 | Segemuchi et al. | 2/449 X |
| 4,726,075 | 2/1988 | Hinrichs | 2/449 X |
| 4,951,322 | 8/1990 | Lin | 2/441 X |
| 5,098,180 | 3/1992 | Tobey | 351/92 X |

FOREIGN PATENT DOCUMENTS

| | | |
|---|---|---|
| 61-160422 | 10/1986 | Japan . |
| 61-206918 | 12/1986 | Japan . |
| 64-70048 | 3/1989 | Japan . |
| 1-12244 | 4/1989 | Japan . |
| 4-7817 | 1/1992 | Japan . |
| 0330725 | 6/1930 | United Kingdom ........... 2/451 |

Primary Examiner—Peter Nerbun

[57] ABSTRACT

A pair of sunglasses and goggles incorporating two functions are provided. A pair of sunglasses comprising a frame member (1) and a lens member (20) can be turned to goggles by detachably attaching an upper goggle frame member to an upper side of the lens member (20), and detachably attaching a lower goggle frame member (40) to a lateral side and lower side of the lens member.

12 Claims, 19 Drawing Sheets

GOGGLES AND SUNGLASSES

TECHNICAL FIELD

The present invention relates to a pair of goggles and sunglasses that can be used as sunglasses as well as goggles.

BACKGROUND ART

Conventionally, sunglasses and goggles have been separately specified and used for respective applications as sunglasses or as goggles, and none of them has been applicable for both purposes.

In skiing, although sunglasses have been conventionally used for avoiding sunburn, and goggles for protection against snow, wind and the like, it has been annoying that two items, sunglasses and goggles, must be carried.

Hence, it is an object of the invention to provide one item that can be used for both purposes.

DISCLOSURE OF THE INVENTION

Thus, in order to provide functions of both sunglasses and goggles in one item, the present invention presents a pair of sunglasses comprising a frame member 1 and a lens member 20, and arranged to be turned into a pair of goggles by detachably attaching an upper goggle frame member 30 to an upper side of the lens member 20 or the frame member 1, and a lower goggle frame member 40 to a lateral side and lower side of the lens member 20 or the frame member 1.

Additionally, in the arrangement, an integrated goggle frame member is formed by connecting both ends of the upper goggle frame member 30 with both ends of the goggle frame member 40.

In the goggle frame member comprising the two parts or the integrated goggle frame member, the lower goggle frame member 40 corresponding to both lateral sides of the lens member 20 or frame member 1 is extended in the longitudinal direction of temples of the sunglasses to form cheek side covering parts 50, respectively, so that the face is covered in the side surface of cheeks respectively by the cheek side covering parts 50.

On the other hand, the invention presents a pair of sunglasses comprising a frame member 1 and a lens member 20, and arranged to be turned into a pair of goggles by detachably attaching a lower goggle frame member 40 to a lateral side and lower side of the lens member 20 or frame member 1, and cheek side covering parts 50 to a lateral side of the lens member 20 and/or frame member 1.

Moreover, in the arrangements, the lens member 20 is detachable attached to the frame member.

The sunglasses are turned into goggles by attaching the upper goggle frame member 30 to the upper side of lens member 20 or frame member 1 of the sunglasses, and attaching the lower goggle frame member 40 to the lateral side and lower side of the lens member 20.

They can be easily turned into goggles by attaching the integrated goggle frame member to the lens member and frame member.

The sunglasses are turned into goggles by attaching the upper goggle frame member 30 to the upper side of lens member 20 and frame member 1 of the sunglasses, the lower goggle frame member 40 to the lateral side or lower side of the lens member 20, and the cheek side covering part 50 to the lateral side of lens member 20 and/or the frame member 1. Thus, a pair of goggles are easily obtained by attaching the goggle frame members to the sunglasses, and serve for protection against snow, winds and the like.

Furthermore, by extending the cheek side covering parts 50 to the lower goggle frame member 40 or separately attaching the cheek side covering parts 50 to the lens member 20 and/or frame member 1, the effect of protection against snow, winds and the like is further increased.

In addition, the goggles are turned into sunglasses by removing the goggle frame members.

Thus, according to the invention, both sunglasses and goggles are presented as main subjects, respectively, in either form, rather than either a pair of sunglasses or goggles as a main subject.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The embodiments of the present invention are described below by referring to the attached drawings. All drawings show embodiments of the invention.

Figure 1:
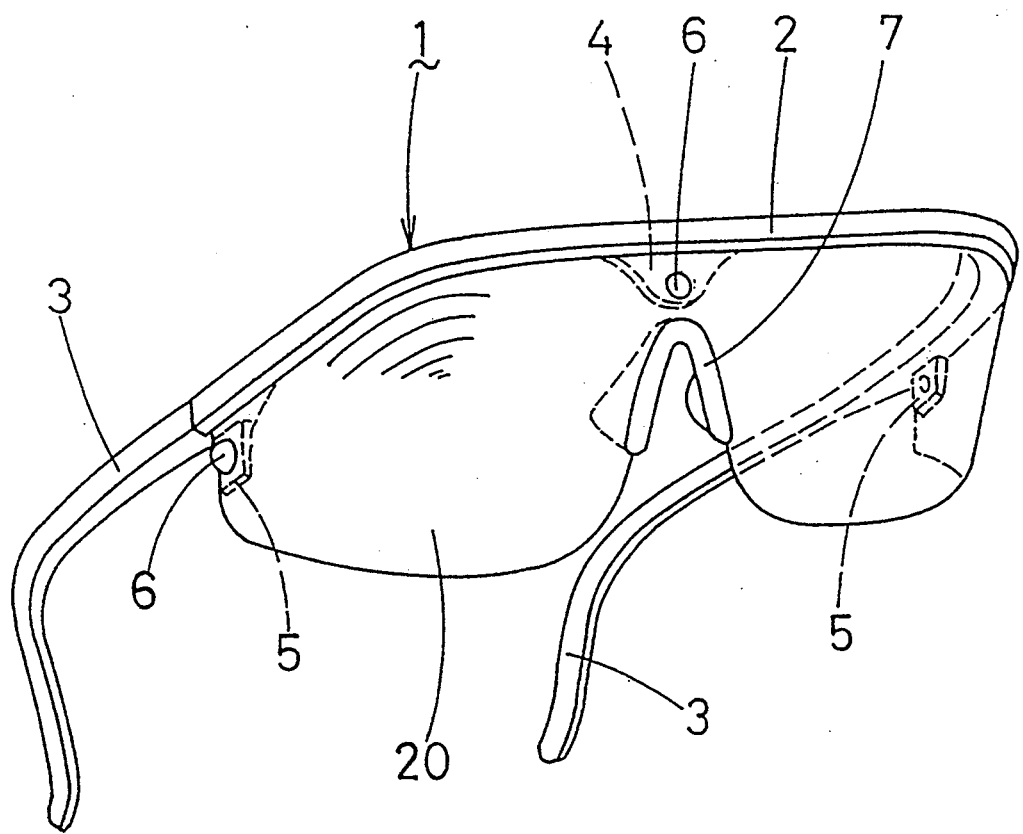
FIG. 1 is an overall perspective view showing a form of sunglasses of an embodiment of the invention.

In FIG. 1, the invention in a state of sunglasses is shown in an overall perspective view, and comprises a frame member 1 and a lens member 20, wherein the lens member 20 is detachably attached to the frame member 1. The frame member 1 comprises a main frame part 2 supporting an upper side of the lens member 20, and temples 3, 3 rotatably attached to both ends of the main frame part 2. In the embodiment, a nose pad 7 is also detachably attached to a joint part of right and left lenses of the lens member 20. The nose pad 7 may be formed extendingly from the central part downwardly of the frame member 1 so as to be formed integrally with the frame member 1.

In order to combine the components, firstly, the upper side of lens member 20 is engaged in a groove part provided in a lower surface of the main frame part 2. A hole formed in the center and cutout parts in both ends of the upper side of the lens member 20 is matched with respective holes formed in support parts 4, 5, 5 that extend downwardly in the center and both ends of the main frame part 2, and fixed to them by pins 6 of a synthetic resin. Finally, the nose pad 7 is engaged with the central part of lens member 20 from therebelow, and a pair of sunglasses are completed.

Incidentally, by forming the frame member 1 in an appropriate size, the support parts 4, 5, 5 may be eliminated so that the synthetic resin pins 6 can be directly engaged with the frame member 1. Alternatively, instead of engaging them by the pins 6, a convex part may be provided on either one of the frame member or the lens member, and a concave part on the other, so that the lens member can be fixed by mutual engagement thereof.

Figure 2:
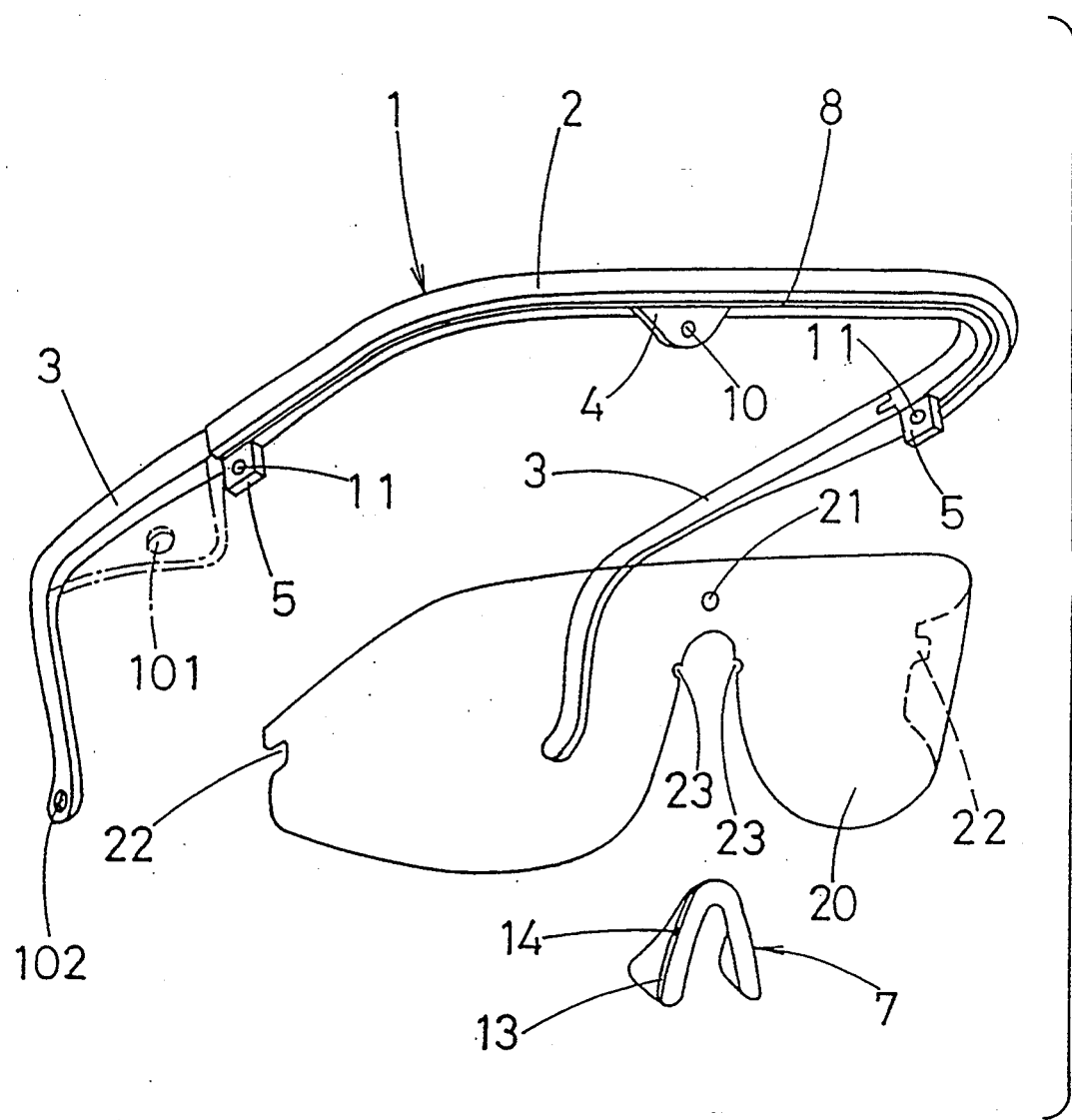
FIG. 2 is an exploded perspective view of FIG. 1.

FIG. 2 is an exploded perspective view of the sunglasses shown in FIG. 1, a groove part 8 is provided in the main frame part 2 of frame member 1 in the lower surface thereof. The groove part 8 is formed over the lower surface of main frame part 2 between both ends thereof. The upper side of lens member 20 can be engaged in the groove part 8. In the center of main frame part 2, the support part 4 is extended downwardly, and provided with a hole 10. In the lower surface of main frame part 2, the support parts 5, 5 are extended downwardly, in both ends thereof, and provided with a hole 11. The number and location of the support parts may be selected optionally. As a material of the frame member 1, a synthetic resin with superior flexibility is employed.

As shown in a chain line in FIG. 2, base part of a temple 3 may be formed so as to protrude in the lower direction, and holes 101, 102 may be formed in the protruded part and a leading end of the temple 3. By utilizing the holes 101, 102, and providing a resilient band between the ring and left temples 3, 3, the sunglasses can be more securely fixed to the face by means of the resiliency. Here, by forming the holes 101, 102 in plural locations, the fixing position of the band may be changed, and the fixing strength can be adjusted.

For the lens member 20, a synthetic resins lens colored for sunburn is used, molded in such shape that an upper side thereof is consistent with the groove part 8, and a hole 21 is formed through the upper side in the center. The hole 21 is consistent with the hole 10 in the support part 4 of main frame 2. Although a concave part cut out of the upper side of the lens may be employed alternatively to the hole 21, in order to securely prevent the lens from falling off, it is preferable to form a concave part in a shape such as a ¾ arcuate shape, rather than a U shape, that it has a holder portion to hold the lens.

In both upper side parts of the lens member 20, cutout parts 22, 22 are formed. The cutout parts 22 are fitted to holes 11, 11 of the support part 5, 5 formed at both ends in the lower surface of the main frame 2. Although a through hole may be employed in place of the cutout part 22, considering attachment of a lower goggle frame member 40 described hereinafter, such method as employed in the embodiment is preferable. Cutout parts 23, 23 are also provided in a part that engages with the nose pad 7.

For the nose pad 7, a soft synthetic resin having a superior resiliency is employed, and a groove part 13 is provided over an entire circumference thereof, and engaged with a joint part of right and left lenses of the lens member 20 in the edge thereof from the lower direction. A projection 14 is formed appropriately in two positions within the groove 13, and is matched with the cutouts 23, 23 of lens member 20. In this way, the nose pad is prevented from dropping off. The projection 14 and the cutoff 23 are optionally structured.

In assembling a pair of sunglasses thus structured, firstly, the upper side of lens member 20 is engaged in the groove part 8 in the lower surface of main frame part 2, then, the hole 21 and cutout parts 22, 22 are matched with the holes and 11, 11 provided in the support parts 4 and 5, 5 of main frame part 2, and fixed by pins 6 made of synthetic resin. Further, the groove part 13 of nose pad 7 is engaged with the lens member 20, and the projections 14, 14 are matched with the cutouts 23, 23 for fixing.

By structuring a pair of sunglasses in such manner, the lens member 20 can be easily replaced with a lens member of other colors.

On the other hand, the components of the sunglasses may be optionally formed stationarily rather than detachably, in such case, the lens member 20 may be adhered to the frame member 1 by means of an adhesive, and the support parts 4, 5 of frame member 1 and the hole 21 and cutout 22 of the lens member 20 may be eliminated. In addition, the cutout 23 and the projection 14 for fixing the nose pad 7 may be also eliminated.

Figure 3:
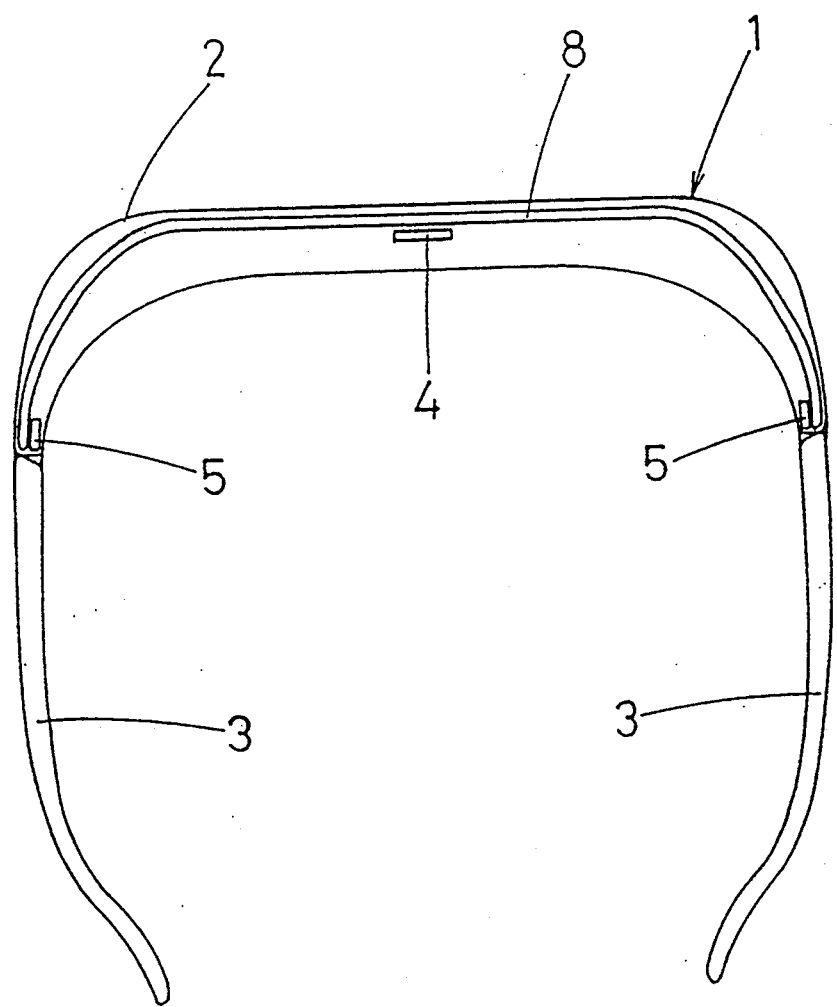
FIG. 3 is a bottom view showing a frame member of an embodiment of the invention.

FIG. 3 is a bottom view of the frame member 1. The main frame part 2 is formed to have an appropriate width, curved in the side of face so as to correspond with the face surface in either ends thereof, and the temples 3,3 are rotatably attached at both ends. In the lower surface of main frame part 2, the groove part 8 is formed over an entire range between both ends. The groove part 8 has a width approximately same as a thickness of the lens member 20. The support parts are indicated by numerals 4 and 5, 5.

Figure 4:
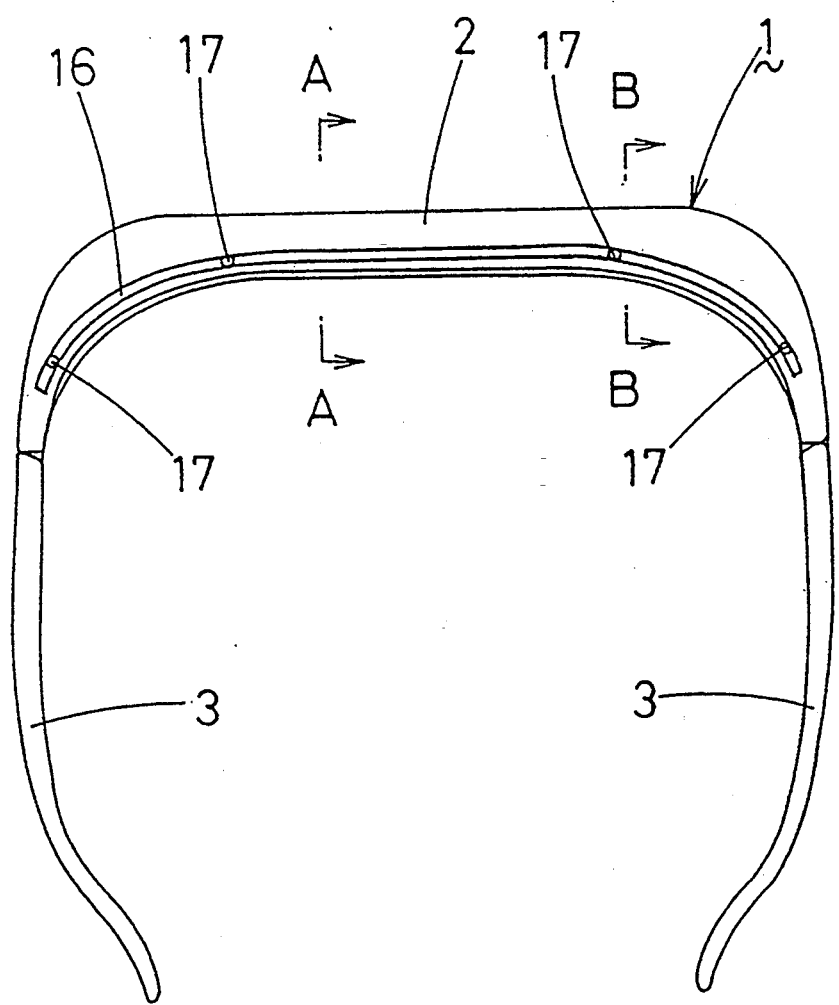
FIG. 4 is a plan view showing a frame member of an embodiment of the invention.

FIG. 4 is a plan view of the frame member 1. In the upper surface of main frame part 2, a groove part 16 is formed over approximately entire range between the both ends thereof, and a perforation 17 is formed in four locations within the groove part 16. The number of perforations 17 can be optionally determined. An upper goggle frame member 30 described hereinbelow can be attached to the groove part 16 and perforations 17. On the other hand, rather than forming the perforations 17, the groove part 16 may be optionally provided appropriately with several points where the groove is eliminated, so that only the groove part 16 is intermittently formed.

Figure 5:
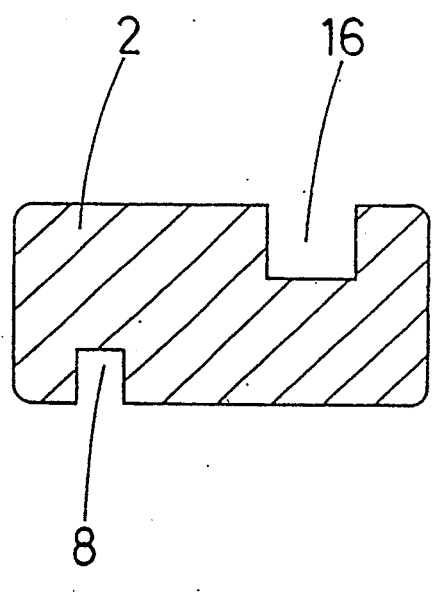
FIG. 5 is an end view taken along a line A—A of FIG. 4.

FIG. 5 is an end view taken along a line A—A of FIG. 4, and shows formation of the groove part 16 in the upper surface of main frame part 2 and the groove 8 in the lower surface thereof. An upper goggle frame member 30 described hereinbelow is attached to the groove part 16, and the upper side of lens member 20 is engaged in the groove part 8.

Figure 6:
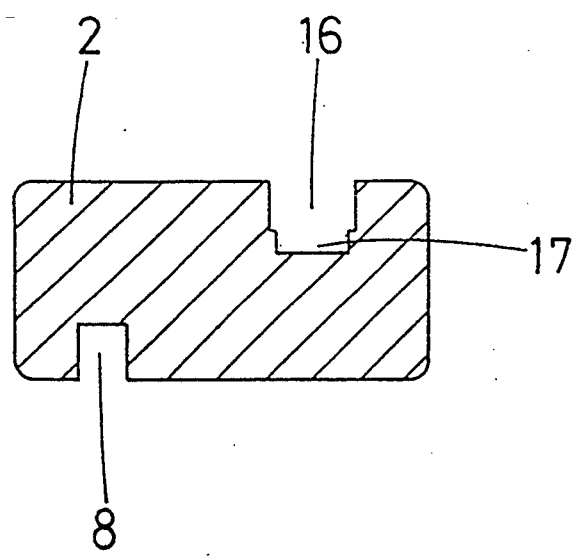
FIG. 6 is an end view taken along a line B—B of FIG. 4.

FIG. 6 is an end view taken along a line B—B of FIG. 4, and shows formation of the groove part and perforations 17 in the upper surface of main frame part 2 and the groove part 8 in the lower furface thereof. The perforations 17 may be formed through the lower part.

Figure 7:
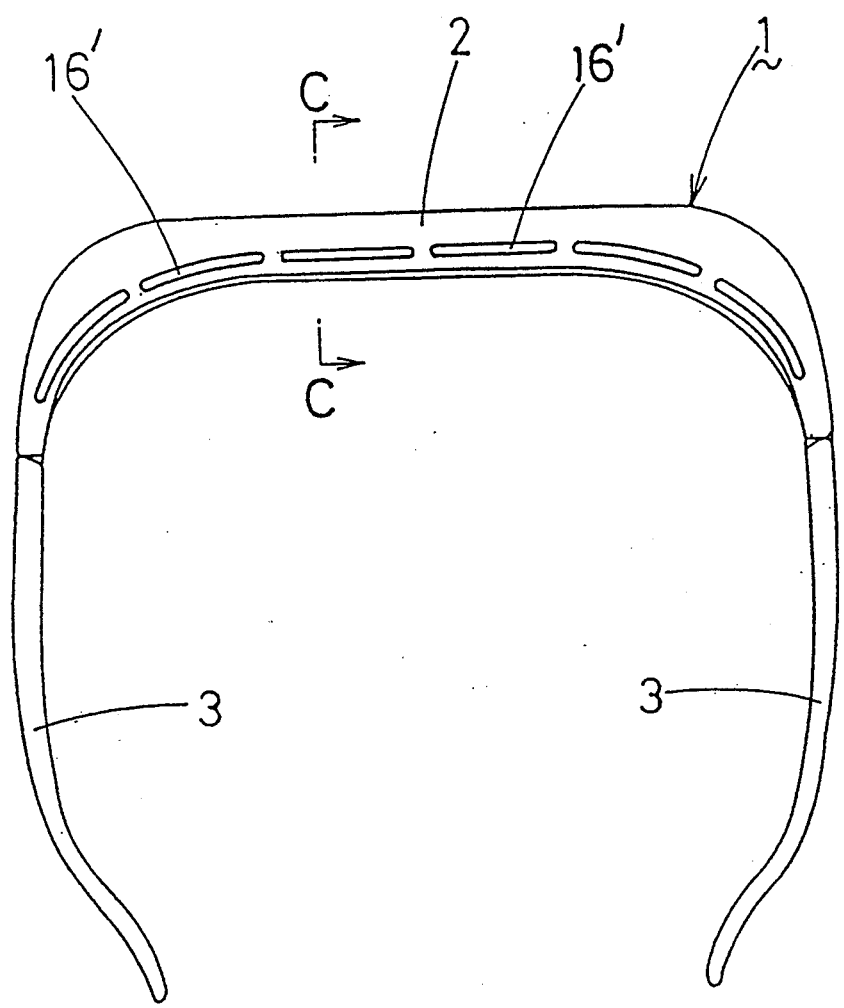
FIG. 7 is a plan view showing a frame member of another embodiment of the invention.
Figure 8:
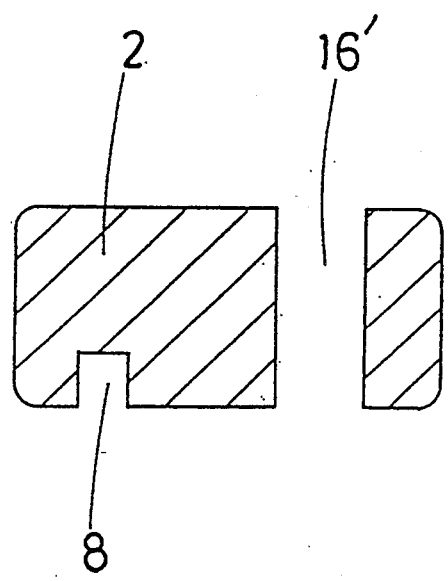
FIG. 8 is an end view taken along a line C—C of FIG. 7.
Figure 17:
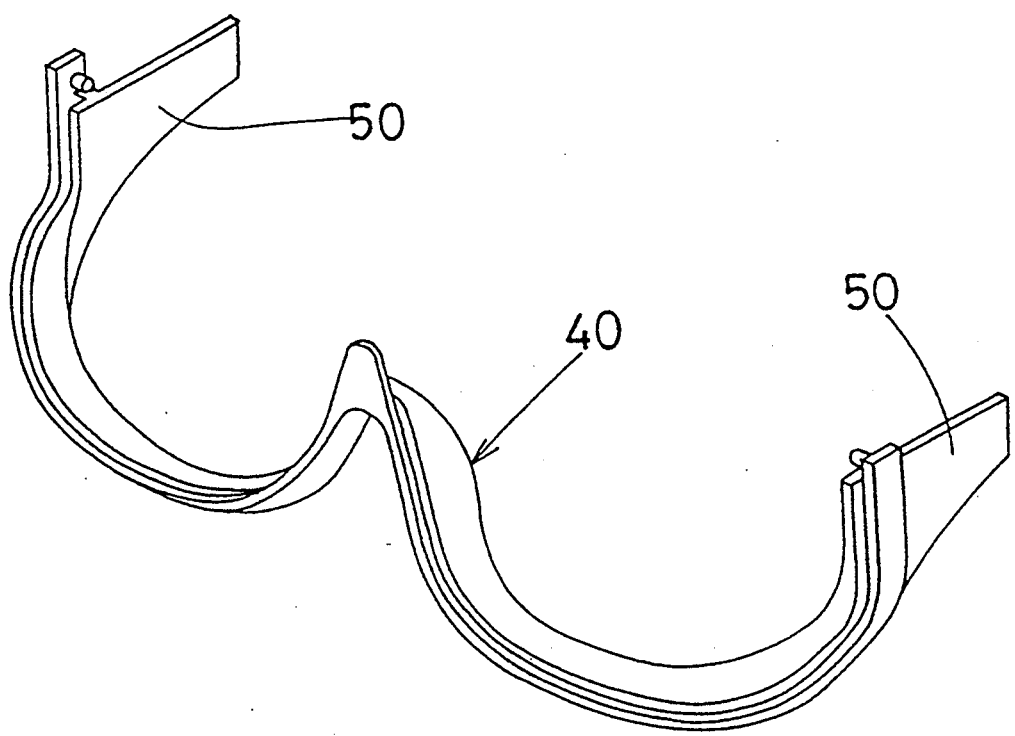
FIG. 17 is a perspective view showing another embodiment of a lower goggle frame member of the invention.

FIG. 17 is a plan view of a frame member 1 of another embodiment. A groove part provided in the frame part 1 has a shape different from that of the embodiment already described. In this embodiment, the groove part is formed by plural slots 16', and provided intermittently over an approximately entire range between both ends of the main frame part 2. Therefore, as in FIG. 8 showing an end view taken along a line C—C of FIG. 7, the slot 16' is formed by a hole vertically passing through. The upper side of lens member 20 is to be engaged in the groove part 8.

Figure 9:
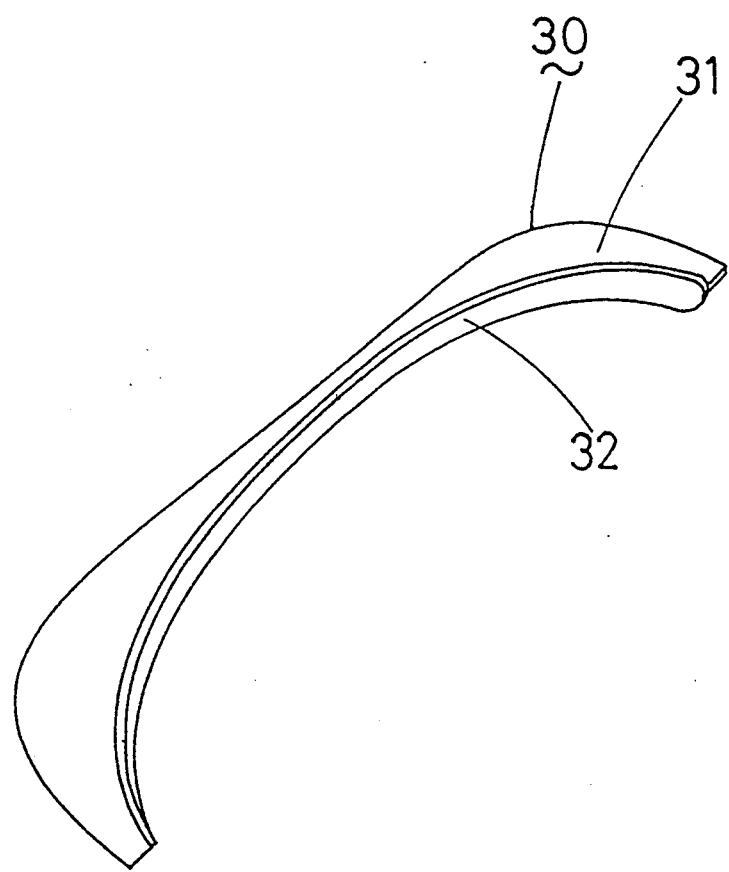
FIG. 9 is a perspective view showing an upper goggle frame member of an embodiment of the invention.

FIG. 9 is a perspective view of the upper goggle frame member 30 looking perspectively from the upper direction, which is formed by a soft synthetic resin. The upper goggle frame member 30 can be attached to the upper surface of main frame part 2 of the frame member 1 shown in FIG. 4, has approximately the same shape as that of the main frame part 2, and is formed flatly in a upper surface 31 thereof. On a side corresponding to the face surface of the upper surface 31, a front abutment part 32 is vertically extended in the edges of upper surface 31 on the facial side.

Figure 10:
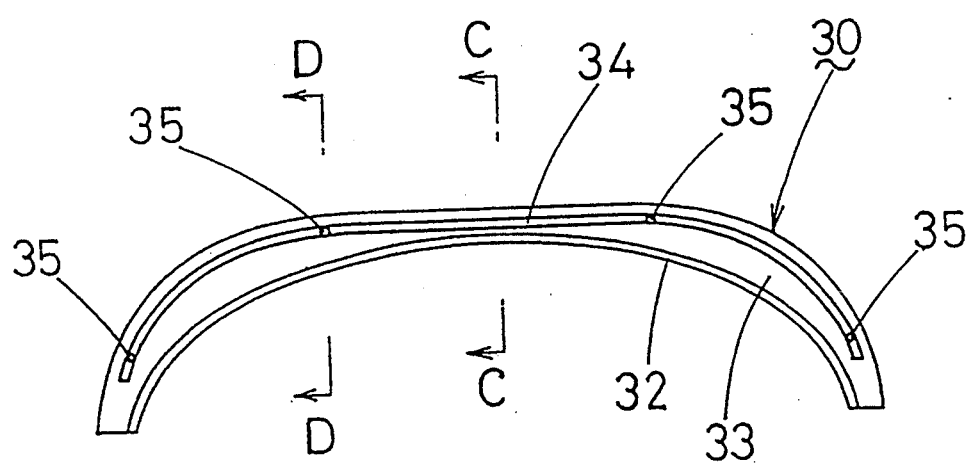
FIG. 10 is a bottom view showing an upper goggle frame member of an embodiment of the invention.

FIG. 10 is a bottom view of the upper goggle frame member 30. In a lower surface 33 of the upper goggle frame member 30, a convexed strip 34 is formed over an approximately entire range between both ends thereof so that it can be engaged in the groove part 16 and perforations 17 in the upper surface of main frame part 2, and a projection 35 in four locations. The front abutment part is indicated by numeral 32, and formed in the direction perpendicular to the drawing, that is, perpendicular to the lower surface 33.

Figure 11:
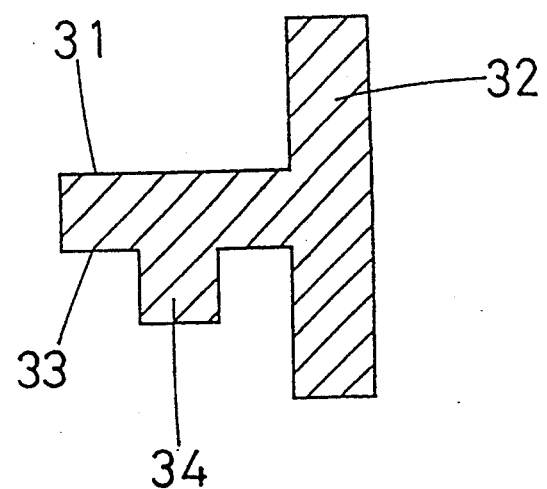
FIG. 11 is an end view taken along a line C—C of FIG. 10.

FIG. 11 is an end surface of the upper goggle frame member 30 shown in FIG. 10 along a line C—C, wherein the upper surface 31 and lower surface 33 are formed so as to be perpendicular to the front abutment part 32, and the convexed strip 34 is formed projecting downwardly in the lower surface 33.

Figure 12:
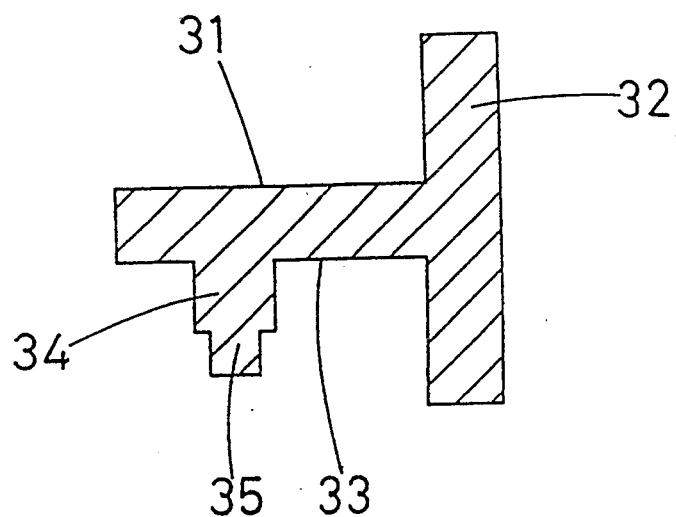
FIG. 12 is an end view taken along a line D—D of FIG. 10.

FIG. 12 also shows an end surface along a line D—D of FIG. 10, wherein a projection 35 is formed in the leading end of the convexed strip 34.

Figure 13:
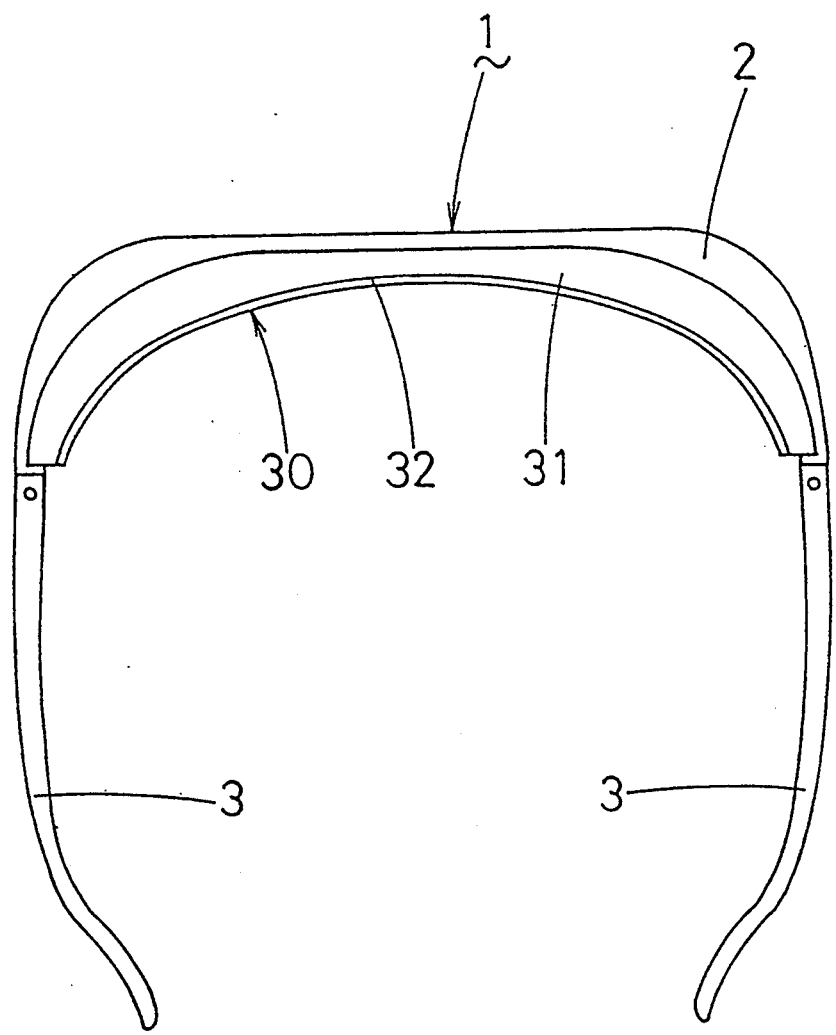
FIG. 13 is a plan view showing an upper goggle frame member attached to a frame member of an embodiment of the invention.

FIG. 13 is a plan view showing attachment of the upper goggle frame member 30 to the frame member 1.

By attaching the upper goggle frame member 30 to the frame member 1 in the upper surface of main frame part 2, the main frame part 2 is somewhat extended on the front side, and the front abutment part 32 can be sufficiently abutted to the face in front. Owing to the convexed strip 34 and projection 35 formed in the lower surface 33 of upper goggle frame member 30, prevention of horizontal offsetting of the upper goggle frame member 30 is ensured, when the goggles are worn.

Figure 14:
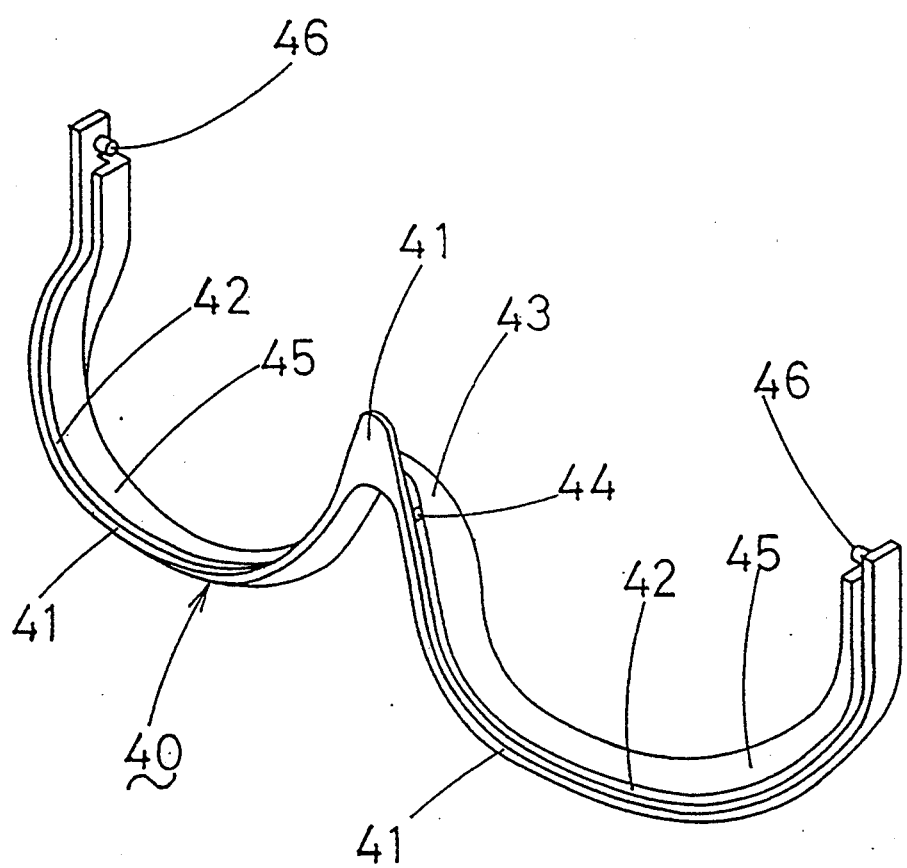
FIG. 14 is a perspective view showing a lower goggle frame member of the invention.

FIG. 14 is a perspective view of the lower goggle frame member 40 looked perspectively from upper front. The lower goggle frame member 40 has a shape approximately consistent with that of the lateral side and entire lower side of the lens member 20. Along a front surface 41 of the lower goggle frame member 40, a slit groove 42 is formed over an entire range between both ends thereof. A projection 44 can be formed within the slit groove 42 formed in a nose pad part 43 of the frame member 40, and fitted to the cutout 23 of lens member 20. In addition, a cheek abutment part 45 on the facial side of the lower goggle frame member 40 is extended toward the cheek side so that it is sufficiently abutted to the cheek. Moreover, in both ends of the lower goggle frame member 40, convex parts 46, 46 are employed in positions corresponding to the holes 11, 11 of support parts 5, 5 provided in both ends of the main frame part 2. In order to attach the lower goggle frame member to the sunglasses, the nose pad 7 is removed from the lens member 20, and the pins 6, 6 from both ends of the main frame 2, then, the lower goggle frame member 40 is engaged with the lateral side and the entire lower side of lens member 20. In this operation, the convex parts 46, 46 in both ends of the lower goggle member 40 should be matched with the cutouts 22, 22 provided in the upper part of the lateral side of the lens member 20. Moreover, the lower goggle frame member 40 can be attached to the sunglasses by engaging the convex parts 46, 46 in the holes 11, 11 of support parts 5, 5 in both ends of the main frame part 2.

In a pair of sunglasses integrally formed with the nose pad 7, the nose pad 43 can be eliminated from the lower goggle frame member 40, and the lower goggle frame member 40 may be structured only by the front surface 41 in that part. However, considering the strength of the lower goggle frame member 40 and sufficient adhesion to the face, the structure shown in the embodiment is more preferable.

Figure 15:
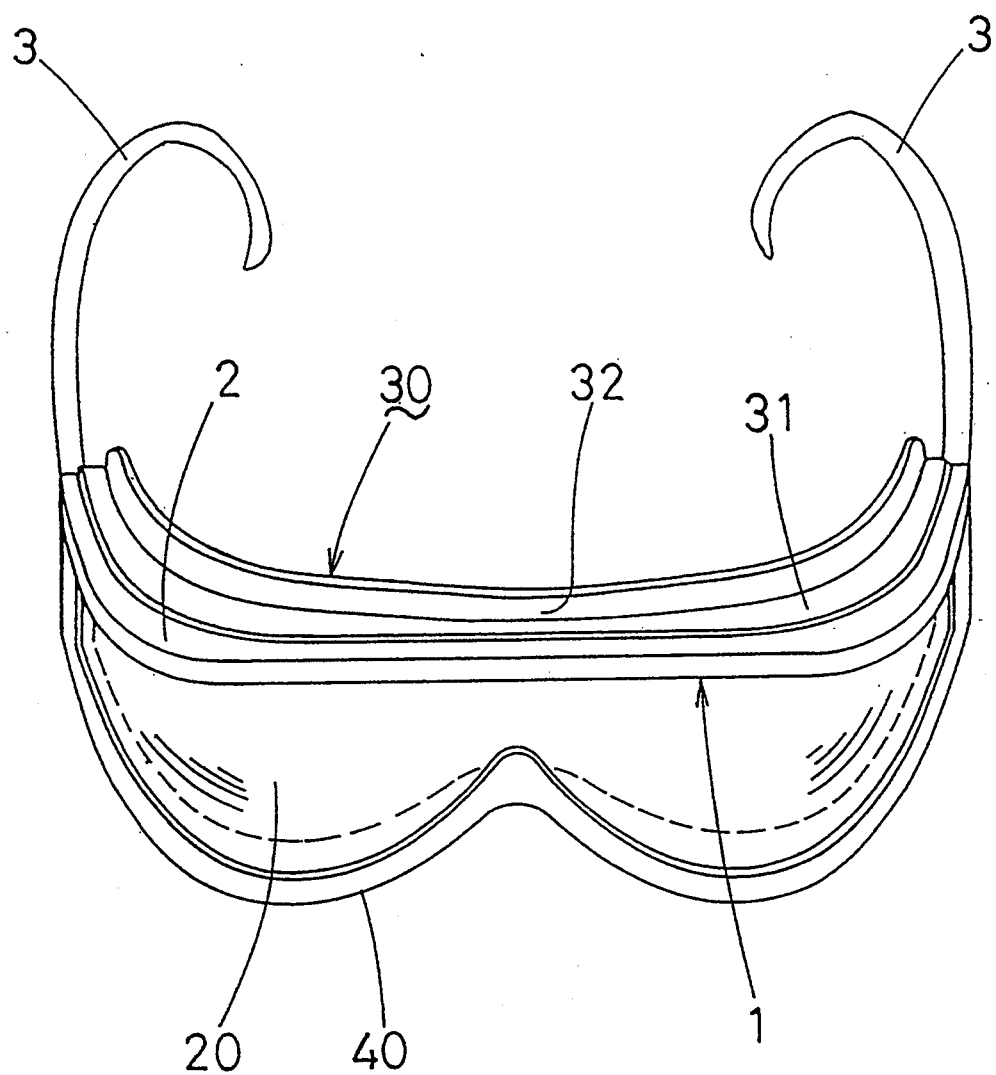
FIG. 15 is an overall perspective view showing a form of goggles of an embodiment of the invention from the upper front direction.

FIG. 15 is a perspective view of the invention viewed from the upper front direction. The upper goggle frame member 30 is attached to the upper surface of main frame part 2, and the lower goggle frame member 40 to the lens member 20 and the main frame part 2, thus, forming a pair of goggles.

Figure 16:
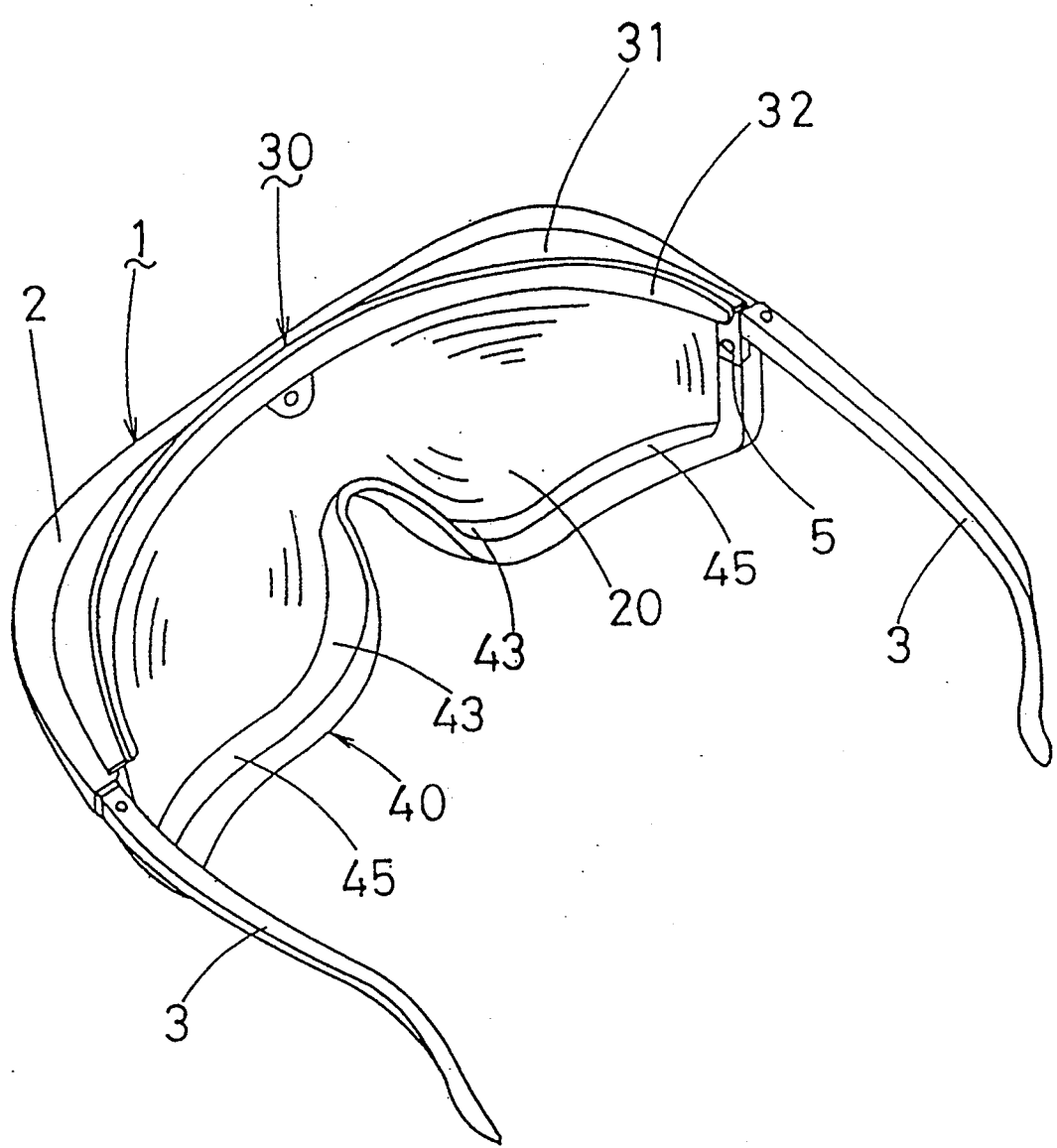
FIG. 16 is an overall perspective view showing a form of goggles of an embodiment of the invention from the upper rear direction.

FIG. 16 is also a perspective view of the invention viewed perspectively from the upper rear direction. The upper goggle frame member 30 and the lower goggle frame member 40 are respectively attached to the sunglasses, the front abutment part 32 of upper goggle frame member 30 and nose pads 43, 43 and cheek abutment parts 45, 45 of the lower goggle frame member 40 (the cheek abutment part 45 of lower goggle frame member 40 engaged with the lateral side of lens member 20 included) are all adhered sufficiently to the front, nose and cheeks of the face, and functions of goggles can be sufficiently obtained. Incidentally, the front abutment part 32 of upper goggle frame member 30 and the nose pads 43, 43 and cheek abutment parts 45, 45 of the lower goggle frame member 40 may be provided with a cushioning material such as sponge.

Figure 18:
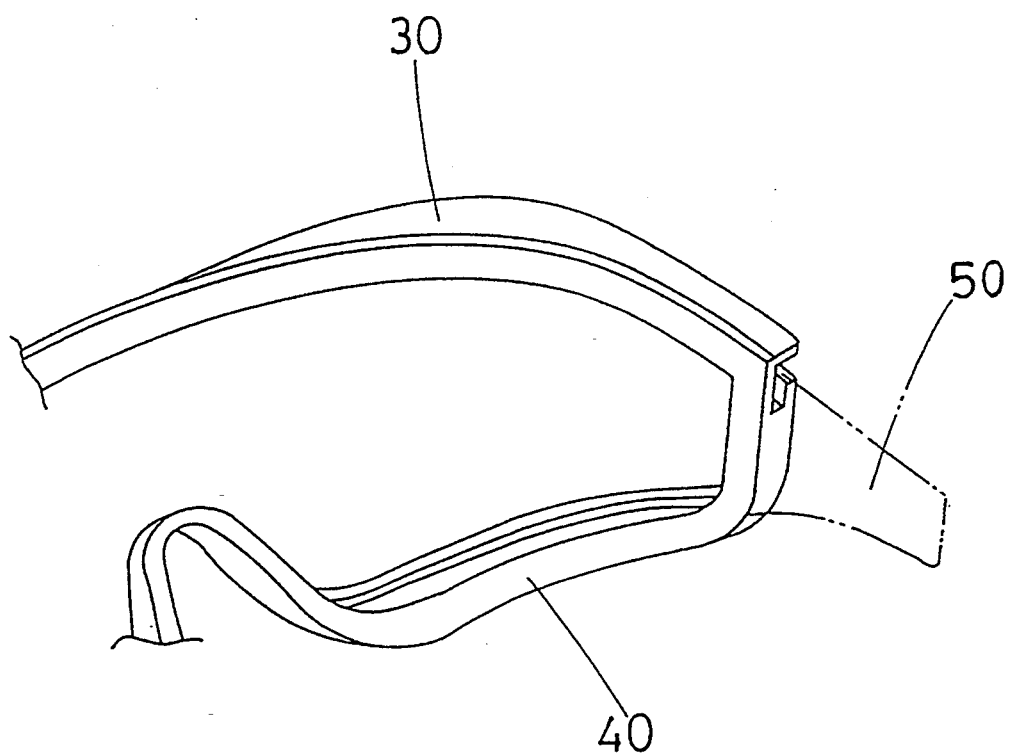
FIG. 18 is a partially cutaway perspective view explaining the other goggle frame member of the invention.

FIG. 17 is a perspective view showing another embodiment of lower goggle frame member 40, wherein cheek abutment parts 45 in both ends of the frame member 40 are extended in the longitudinal direction of temples to form cheek side covering parts 50. By the cheek side covering parts 50, the lower goggle frame member 40 can be more perfectly adhered to the face in the side surface of the cheeks as well. FIG. 18 is a partially cutaway perspective view explaining the other embodiment of the goggle frame member, where an upper goggle frame member 30 and lower goggle frame member 40 are, in this embodiment, attached at both ends, respectively, in such manner that both of them are integrally formed. In the embodiment, the goggle frame member is consisted of one component, and such problem of being lost as an accessory of sunglasses is reduced.

Moreover, in this goggle frame member, similarly as the embodiment shown in FIG. 17, parts corresponding to the lateral sides of lens member may be extended in the longitudinally direction of temples to form a cheek side covering part 50. By the cheek side covering part 50, the goggle frame member can be more perfectly adhered to the face in the side surface of cheeks.

Figure 19:
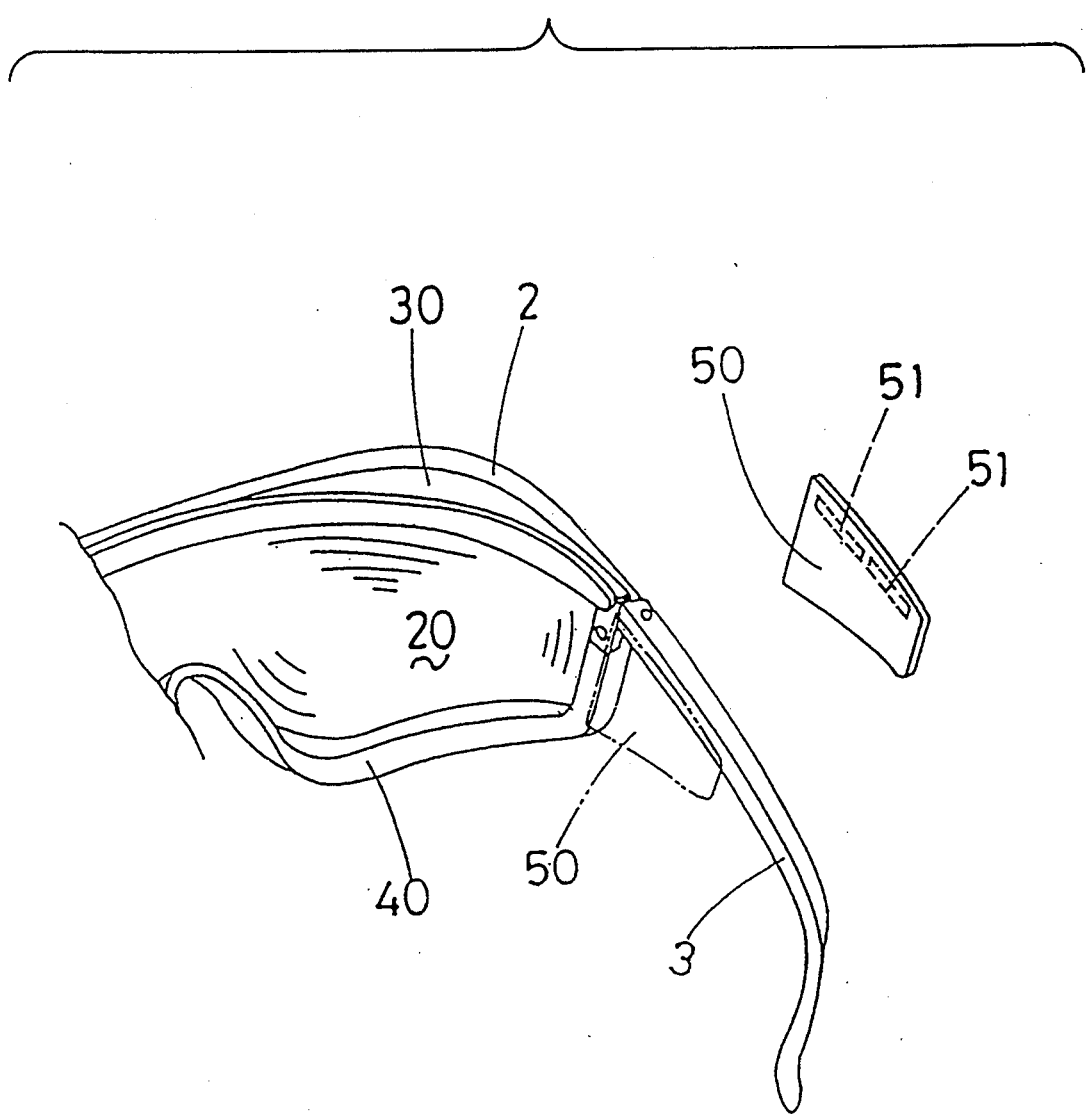
FIG. 19 is a view explaining still other embodiment of goggle frame member of the invention.

FIG. 19 is a view explaining still other embodiment of goggle frame member that is consisted of three components, and upper goggle frame member 30, a lower goggle frame member 40 and a cheek side covering part 50. The cheek side covering part 50 is formed by a plate-like material having an appropriate shape for more complete sealing of spacings between the lateral sides of lens member 20 and temples 3, and a convexed strip 51 not shown that can be fitted in a groove part formed in the main frame part of frame member 1 and/or temple 3 is employed in one of the surfaces. The convexed strip 51 is engaged in the groove part provided in the main frame part 2 and/or temple 3, and fixed. It is entirely optional to form the cheek side covering part 50 so as to be attachable to the lens member 20 or lower goggle frame member 40.

In addition to the embodiments, the invention can be realized in such various modifications that the frame member can be adapted to support the entire circumference of the lens member instead of supporting the upper side of the lens member only. In this case, the lower goggle frame member can be fixed only to the frame member. On the contrary, when such lens member as in the embodiment is employed, the frame member may be possibly changed in shape so as to support only both ends, that is, right and left ends of the lens member, then, the upper goggle frame member can be fixed only to the lens member by changing it to have a groove engaged with the upper side of the lens member. It is sufficient as far as the upper goggle frame member and the lower goggle frame member are attached to at least either one of the frame member and lens member. And the attachment can be achieved by appropriately combining such methods as engaging a pin or projection to a hole or cutout, and forming a groove in either one of the frame member and lens member and fitting the other member in the groove.

Additionally, although a single lens member with the right and left parts combined together is used in the embodiments, lens members separated in right and left parts may be also employed.

As for applications, the invention can be used also for measures against dust and pollinosis in addition to sports such as skiing.

With the above construction, the invention enables combining the two functions of sunglasses and goggles in one item.

Accordingly, the present invention eliminates the necessity of carrying two items, providing convenience of carriage.

In using them by turning from sunglasses to goggles, or contrarily from goggles to sunglasses, they can be easily transformed to either sunglasses or goggles only by attaching or detaching the goggle frame members.

Moreover, according to the invention, in the form of goggles, the entire goggle frame part formed by the goggle frame members is sufficiently adhered to the face.

In the case of the goggle frame member with cheek side covering parts, the goggle frame members can be more perfectly adhered to the side surface of the cheeks.

In the case of the lens member of detachable structure, it can be easily replaced with a lens member of different color, permits a total coordination with different outfits, and enhances fashionability.

Thus, the invention is superior in practicability, and provides very remarkable effects.

INDUSTRIAL APPLICABILITY

Accordingly, sunglasses and goggles of the invention have the two functions of sunglasses and goggles in one item. They are, therefore, very useful as goggles for sports, or measures against dusts and pollinosis, and also applicable for daily use as sunglasses.

I claim:

1. In combination a pair of sunglasses and goggle frame portions comprising:
    a pair of sunglasses including:
        a frame member having two temples; and
        a lens member connected to said frame member;
    an upper goggle frame member attachable and detachable to an upper portion of said pair of sunglasses, said upper goggle frame member extends completely across said upper portion of said pair of sunglasses and having a front abutment part for abutting against a user's forehead;
    a lower goggle frame member attachable and detachable to a lower portion of said pair of sunglasses, said lower goggle frame member extends completely across said lower portion of said pair of sunglasses and having a cheek abutment part;
    wherein said pair of sunglasses, said upper goggle frame and said lower goggle frame combine to form a pair of goggles, whereby said pair of sunglasses, said upper goggle frame member and said lower goggle frame member form a substantially closed space when placed on a user's face.

2. The combination of sunglasses and goggles according to claim 1, wherein the upper goggle frame member and the lower goggle frame member are attachable and detachable to each other at both ends to form an integral goggle frame member.

3. The combination of sunglasses and goggles according to claim 1, wherein the lower goggle frame member corresponding to both lateral sides of the pair of sunglasses is extended in a longitudinal direction of the temples of the frame member to form cheek side covering parts, respectively, and the respective cheek side covering parts are arranged so as to cover the face in the side surface of the cheeks.

4. The combination of sunglasses and goggles according to claim 1, wherein the lens member is detachably attached to the frame member.

5. The combination of sunglasses and goggles according to claim 2, wherein the lower goggle frame member corresponding to both lateral sides of the pair of sunglasses is extended in the longitudinal direction of the temples of the frame member to form cheek side covering parts, respectively, and the respective cheek side covering parts are arranged so as to cover the face in the side surface of the cheeks.

6. The combination of sunglasses and goggles according to claim 2, wherein the lens member is detachably attached to the frame member.

7. The combination of sunglasses and goggles according to claim 3, wherein the lens member is detachably attached to the frame member.

8. The combination of sunglasses and goggles according to claim 1, wherein the upper goggle frame member is detachably attached to an upper side of said frame member.

9. The combination of sunglasses and goggles according to claim 1, wherein said lower goggle frame member is detachably attached to lateral and lower sides of said lens member.

10. The combination of sunglasses and goggles according to claim 1, further including cheek side covering portions detachably attached at lateral sides of the lens member.

11. The combination of sunglasses and goggles according to claim 10, wherein said cheek side covering portions are attached to said temples of said frame member.

12. The combination of sunglasses and goggles according to claim 10, wherein said cheek side covering portions are attached to said lower goggle frame member.

* * * * *